(12) United States Patent
Lee

(10) Patent No.: US 6,364,852 B1
(45) Date of Patent: Apr. 2, 2002

(54) DEVICE FOR REDUCTION OF THE ANAL CUSHIONS IN THE TREATMENT OF MINOR HEMORRHOIDAL DISEASE

(76) Inventor: Sin Hang Lee, 53 Millan Rd., Woodbridge, CT (US) 06325

( * ) Notice: Subject to any disclaimer, the term of this patent is extended or adjusted under 35 U.S.C. 154(b) by 0 days.

(21) Appl. No.: 09/642,705

(22) Filed: Aug. 17, 2000

(51) Int. Cl.$^7$ .................................................. A61F 13/20
(52) U.S. Cl. ........................... 604/15; 604/12; 604/514; 606/197
(58) Field of Search ................................. 604/500, 514, 604/515, 518, 11–13, 14, 15, 73, 285–288, 328; 128/897, 898; 606/197, 191–194, 196; 600/29–32

(56) References Cited

U.S. PATENT DOCUMENTS

| | | | |
|---|---|---|---|
| 3,675,642 A | * | 7/1972 | Lord |
| 3,894,539 A | * | 7/1975 | Tallent ........................ 128/261 |
| 4,331,151 A | | 5/1982 | Golden ........................ 128/401 |
| 4,421,504 A | * | 12/1983 | Kline |
| 4,563,182 A | * | 1/1986 | Stoy ............................. 604/285 |
| 4,583,542 A | | 4/1986 | Boyd ........................... 128/341 |
| 4,638,806 A | | 1/1987 | Bartlett ........................ 128/400 |
| 4,670,419 A | * | 6/1987 | Uda et al. |
| 4,906,239 A | | 3/1990 | Bruhl ........................... 604/275 |
| 5,178,627 A | | 1/1993 | Hudock ........................ 606/197 |
| 5,192,266 A | | 3/1993 | Wilk ............................. 604/11 |
| 5,263,926 A | | 11/1993 | Wilk ............................. 604/11 |
| 5,800,485 A | | 9/1998 | Trop ............................. 607/105 |
| 5,924,423 A | | 7/1999 | Majlessi ........................ 128/897 |
| 6,024,742 A | | 2/2000 | Tu ................................. 606/41 |

OTHER PUBLICATIONS

Gibbons et al., "Role of Anal Cushions in Maintaining Continence", The Lancet, vol. 1, Apr. 19, 1986, pp. 886–888.

Thorek, Philip, Anatomy in Surgery, Third Edition (Springer–Verlag, 1985), p. 491.

Keighley and Williams, Surgery of the Anus, Rectum and Colon, Second Edition, vol. 1 (R.W.B. Saunders, 1997), p. 354.

Haas, et al., "The Pathogenesis of Hemorrhoids", Dis. Co. & Rect., Jul. 1994, pp. 442–450.

* cited by examiner

Primary Examiner—Richard K. Seidel
Assistant Examiner—LoAn H. Thanh
(74) Attorney, Agent, or Firm—Nash and Titus, LLC (57) ABSTRACT

This invention involves a new device and method for treating hemorrhoids. The device has a substantially cylindrical shape and, at least at one portion, has a diameter of between about 5 mm and about 30 mm. The device is inserted into an anal canal so that it is positioned against at least one displaced anal cushion, and is maintained there for a sufficient time to achieve reduction of the displaced anal cushion.

24 Claims, 3 Drawing Sheets

DEVICE FOR REDUCTION OF THE ANAL CUSHIONS IN THE TREATMENT OF MINOR HEMORRHOIDAL DISEASE

FIELD OF THE INVENTION

The field of this invention relates generally to medical devices and methods for treating hemorrhoid disease, and specifically for reducing the displaced anal cushions associated with hemorrhoid disease.

BACKGROUND OF THE INVENTION

The condition where the blood vessels covered by rectal glandular mucosa and/or by the modified anal squamous epithelium become dilated and protrude as a mass into the anal canal, has been generally referred to as hemorrhoids or piles. Hemorrhoids are thought to be present in at least half of the world's population by the age of 50, and are said to be one of the oldest ills known to man. In fact, it has been recently recognized that hemorrhoids are actually normal features of the human anatomy. Hemorrhoids are now considered to be mucosa-covered arteriovenous pads or cushions that normally bulge into the lumen of the anal canal just above the pecten band. As an individual ages, the connective tissue system supporting and anchoring these vascular plexuses of the anal cushions deteriorates and the hemorrhoids gradually descend within the mucosal wall and down the lumen of the anal canal. When the descending hemorrhoids with poorly supportive and anchoring connective tissues pass the pecten band and beyond the Hilton's line, as often occurring after defecation in older adults, the arteriovenous plexuses may be caught by the constricting lower edge of the internal sphincter. If this happens, the veins in the plexuses become distended because the venous blood cannot escape into the systemic circulation. The vascular anal cushions become increasingly congested, edematous and hypertrophic, and eventually can no longer return to their normal position readily after defecation. This is the basic pathogenesis of hemorrhoidal disease.

In general, there are two types of hemorrhoids: internal and external. Internal hemorrhoids originate from the superior (internal) hemorrhoidal plexus immediately above the pectinate line. By contrast, external hemorrhoids are varicosities of the inferior (external) hemorrhoidal plexus, which lie below the pectinate line. However, because of the communication between the internal and external hemorrhoidal plexuses, most patients have both internal and external hemorrhoids. Traditionally, hemorrhoids projecting into the anal canal are called first-degree; those that prolapse with defecation but reduce spontaneously are called second-degree; those that require manual reduction are called third-degree; and those that cannot be reduced are called fourth-degree.

Hemorrhoids become "hemorrhoidal disease" when at least one, and usually three, anal cushions descend into the anal canal from the normal resting position above the anal canal and do not retract back into the normal position. The resulting compression of the venous channels by the sphincter muscles surrounding the anal canal prevents the venous blood from returning to the systemic circulation and causes persistent dilation of the hemorrhoidal veins, so that symptoms begin manifesting. Common symptoms of hemorrhoidal disease include, for instance, local foreign body irritation sensation, pain, and bleeding. Surface erosion, edema and chronic inflammation due to the secondary bacterial infection of the protruding hemorrhoids are also common causes of symptoms, which can render the modified cutaneous portion of the anal canal extremely sensitive to any foreign body irritants, even the stool in the lower rectum.

Various remedies for hemorrhoidal disease have been tried for the past 5,000 years, and to date there are a number of devices for use in treating this condition. Many devices are designed to push the hemorrhoids protruding from the external anal orifice back into the anal canal. For instance, see U.S. Pat. No. 5,924,423 to Majlessi, U.S. Pat. No. 4,583,542 to Boyd, and U.S. Pat. No. 5,178,627 to Hudock. Most of the devices and methods are ineffective or provide temporary relief only, and do not involve retraction of the anal cushions to their normal anatomical position above the anal canal. Other methods involve invasive or surgical therapy, but this is only considered when various types of medical management have failed since surgery may not produce the expected relief and may yield undesirable complications.

SUMMARY OF THE INVENTION

With the above problems in mind, the inventor has discovered a topical device and method using same to restore the normal anatomic relationship of the components of the anal canal—in particular, the anal cushions-whereby hemorrhoidal disease is effectively treated and symptoms are consequently diminished. Specifically, the invention involves a device that is substantially cylindrical in shape (such as a rod or tube), and has a substantially smooth outer surface. The device is designed to be inserted into the anal canal to induce a high sphincter muscle tension and to create a high pressure between the device and surrounding sphincter, and to push the downward displaced anal cushion(s) back into its normal anatomical position above the anal canal. The device induces the involuntary constricting action of the patient's internal sphincter, and acts as a counter-compressor (that is, counters external sphincter compression) for the patient's voluntary pelvic floor muscle contraction. The added voluntary pelvic contraction by the patient against the device is effective to collapse the distended submucosal and subepithelial venous channels between the inserted counter compressor and the internal sphincter muscle, and the descended vascular anal cushions are pushed up to their normal anatomical resting position above the pecten band (that is, above the anal canal).

This sphincter tension-inducing device for the treatment of hemorrhoidal disease is based on the current understandings of the anatomic-physiologic relationship between the submucosal vascular spaces of the anal canal and the surrounding sphincters. A summary of this relationship is briefly described as follows.

The anal sphincter behaves as a thin elastic tube. On its inner surface there are widely communicating vascular spaces which may be part of the normal hemorrhoidal plexuses in the wall of the anal canal or may be the downward displaced blood channels of the anal cushions. A transient downward displacement of the vascular anal cushions during defecation is a normal physiologic phenomenon. In children and young adults, the displaced anal cushions return to their normal position above the pecten shortly after defecation and the anal canal remains empty and closed. In general, the blood escapes from these vascular spaces into the systemic circulation and the anal cushions are compressed when the anal sphincter pressure increases. In other words, the size of the anal cushions reduces under high sphincter pressure (tension), and increases when the sphincter pressure drops. The tension of the sphincter can only build up when there is an incompressible device, such as a rigid probe, to stretch the smooth muscles of the sphincter. The tension or pressure that can be created by the squeezing action of the sphincter is in proportion to the internal anal diameter maintained by the inserted device. The sphincter tension approaches zero when the anal canal is empty and the patient is at rest. Under the latter condition, the vascular spaces of the anal cushions tend to be filled up with blood, and the cushions become enlarged, normally above the pecten band, thus maintaining anal continence. However, in the patients with hemorrhoidal disease the downward displaced and enlarged anal cushions cannot retract back from the anal canal and act as an incompressible object to the sphincters, which invariably causes an involuntary heightened sphincter tension, thus further constricting the venous channels. The engorged venous channels in turn increase the size of the hemorrhoids, which leads to even higher sphincter tensions. A vicious cycle is thus created in the patients with hemorrhoidal disease with ever-increasing size of the hemorrhoids.

The sphincter tension-inducing device of the present invention is a rod-like or cylindrical rigid device of an appropriate diameter and length serving as an incompressible probe for the anal sphincter muscles to squeeze on in order to increase the pressure between the tension inducer and the sphincter muscles so that blood is forced out of the engorged vascular channels in the wall of the anal canal. With the action of inserting the device up the anal canal from the anal orifice under sphincter tension, the downward displaced anal cushions are pushed up to their normal anatomic position above the pecten band. After an appropriate period of time the device is removed, and the anal canal becomes empty and closed again.

By returning the anal cushions to their normal anatomic position above the pecten band and rendering the anal canal free of foreign bodies (the downward displaced enlarged cushions), normal blood circulation is re-established. Only when the normal blood circulation is restored, the natural local repair processes can take place in the hemorrhoids. The repair processes include, for instance, absorption of the edematous fluid, organization of the extravasated blood (if any), clearing up of the necrotic cell debris (if any), re-epithelilization of any present denuded mucosal surface, and the formation of scar tissue with deposition of newly formed collagen fibers. In most patients with first-, second- and third-degree hemorrhoidal disease, the anal cushions will remain in their normal anatomic position and the venous plexuses of the anal canal remain collapsed after treatment followed by a period of bed rest. The symptom relief in hemorrhoidal disease achieved by this treatment is usually maintained until the next act of defecation which will invariably disrupt the normalcy of this anatomic-physiologic relationship again. Therefore, it may be preferred that the patient schedule, if possible, the regular single daily bowel movement in the evenings and follow the treatment thereafter before bedtime. In this manner, a normal anal canal anatomy is maintained for the most of a 24-hour day while the supportive scar tissue is being formed in the hemorrhoids. Hemorrhoidal disease is known to be aggravated by frequent bowel movements, for example, in patients with chronic diarrhea.

In order that the device effectively move the anal cushions back above the anal canal, it should be sufficiently rigid (that is, not soft or pliable), sufficiently long to reach the anal cushions above the pectinate line, and have a diameter sufficient for counter-compression. For instance, the device is preferably between about 4 cm and about 10 cm long, and the diameter is preferably between about 5 mm and about 30 mm at the portion in contact with the wall of the anal canal. To facilitate easy insertion, preferably the device has a conical-shaped top or leading end.

In a preferred embodiment, the device includes a stopping portion at the bottom or trailing end, that controls the extent of insertion into the anal canal.

In another embodiment, the device has a hollow portion containing lubricant and/or medicament, a top end that is substantially conical in shape with an opening that is in communication with the hollow portion, a bottom end with an opening that is also in communication with the hollow portion, and an injecting implement insertable into the hollow portion through the opening in the bottom end. In this way, the device operates similar to a syringe, where as the device is being inserted into the anal canal the lubricant and/or medicament is injected by the injecting implement through the opening in the top end into the anal canal.

The invention also entails a novel method for treating hemorrhoidal disease whereby at least one anal cushion is swollen and displaced from its normal anatomical position above the anal canal and is at least partially descended into the anal canal. The method comprises the steps of inserting one of the above-described devices into the anal canal so that it pushes at least one anal cushion above the anal canal and back into its normal anatomical position (that is, its resting position above the anal canal). The device induces involuntary constriction of the internal sphincter while serving as a counter-compressor for the contracting action of the voluntary external sphincter muscle. Insertion should be maintained for sufficient time so that internal and external sphincter tension is raised long enough for the blood in the congested submucosal vascular channels to escape (e.g., engorged blood channels in the wall of the anal canal collapse), and swelling is consequently reduced in at least one anal cushion. Usually between about 5 and about 60 minutes is a sufficient time, and preferably between 25 and 35 minutes for most patients. The device is then removed from the anal canal, and preferably the treatment is followed by several hours of bed rest, for example, an overnight sleep in bed. Once swelling is reduced, the anal cushion(s) usually remain in their relative normal anatomic position above the anal canal although downward displacement of hemorrhoids may occur again during the next act of defecation or straining. Repeated daily treatment may be required to achieve fuller or complete symptomatic relief.

In another embodiment, the method comprises inserting a device having a substantially cylindrical shape and a substantially smooth surface into the anal canal so that it pushes at least one anal cushion (and preferably three) above the anal canal into its normal anatomical position. The device in this embodiment has a hollow portion containing lubricant and/or medicament, a top end that is substantially conical in shape with an opening that is in communication with the hollow portion, a bottom end with an opening that is in communication with the hollow portion, and an injecting implement insertable into the hollow portion through the opening in the bottom end. As the device is being inserted into the anal canal, the lubricant and/or medicament is injected by the injecting implement through the opening in the top end into the anal canal. In this way the lubricant/medicament effectively coats the walls of the anal canal, including the crypts of Morgagni. Insertion is maintained for a sufficient time so that the internal and external sphincter tension is raised for the blood in the congested submucosal vascular channels to escape, and swelling is consequently reduced in the anal cushions. At that point, the device is removed from the anal canal, and preferably the treatment is followed by several hours of bed rest, for example, an overnight sleep in bed. Once swelling is reduced, the anal cushion(s) usually remain in their relative normal anatomic position above the anal canal although downward displacement of hemorrhoids may occur again during the next act of defecation or straining. Repeated daily treatment may be required to achieve fuller or complete symptomatic relief.

Preferably, the device in any of its embodiments is coated with an ointment containing lubricants and/or medicaments. For instance, the ointment may contain antibiotics against the various opportunistic pathogenic bacteria to suppress the local infection which often plays a role in the pathogenesis of hemorrhoidal disease.

These methods of treatment are most effective when utilized after each defecation and before bedtime. The user should remain in a horizontal, relaxed position during treatment.

Used properly, the devices and methods of this invention are able to help restore the descended anal cushions to their normal anatomic position above the pecten band, and to reduce the congestion of the submucosal and subepithelial blood vessels in the anal canal.

DETAILED DESCRIPTION OF THE INVENTION

This invention in both its devices and methods is suitable for the treatment of first-, second- and third-degree hemorrhoidal disease before the latter progresses to the advanced stages of disease. In particular, the invention addresses the problem of displaced anal cushions associated with the onslaught of the hemorrhoidal condition, and especially hemorrhoidal disease. Use of this novel device in the method prescribed assists an individual to restore the normal resting anatomic conditions of the anal cushions above the anal canal, in a non-invasive, simple, painless manner.

This invention in its broadest embodiment contemplates a device having a substantially cylindrical shape and a substantially smooth surface, which is suitable for insertion into a human anal canal in such manner that it is capable of inducing involuntary internal sphincter constriction, serving as a counter-compressor for the contraction of the voluntary external sphincter, and pushing or moving at least one displaced anal cushion protruding into the anal canal back into its normal anatomical position above the anal canal. To work most effectively with minimal discomfort for the user, the device should have a diameter of between about 5 mm and about 30 mm at the portion in contact with the wall of the anal canal.

The device may be in the form of a rod or a tube, and should be sufficiently rigid that it is able to push up and hold at least one displaced anal cushion (and preferably all three) in its correct position just above the anal canal. For instance, the device may be constructed of any rigid incompressible material that will not be harmful, toxic or otherwise adverse to a human patient, such as a hard plastic, rubber, metal, re-enforced papers or wood.

Figure 3:
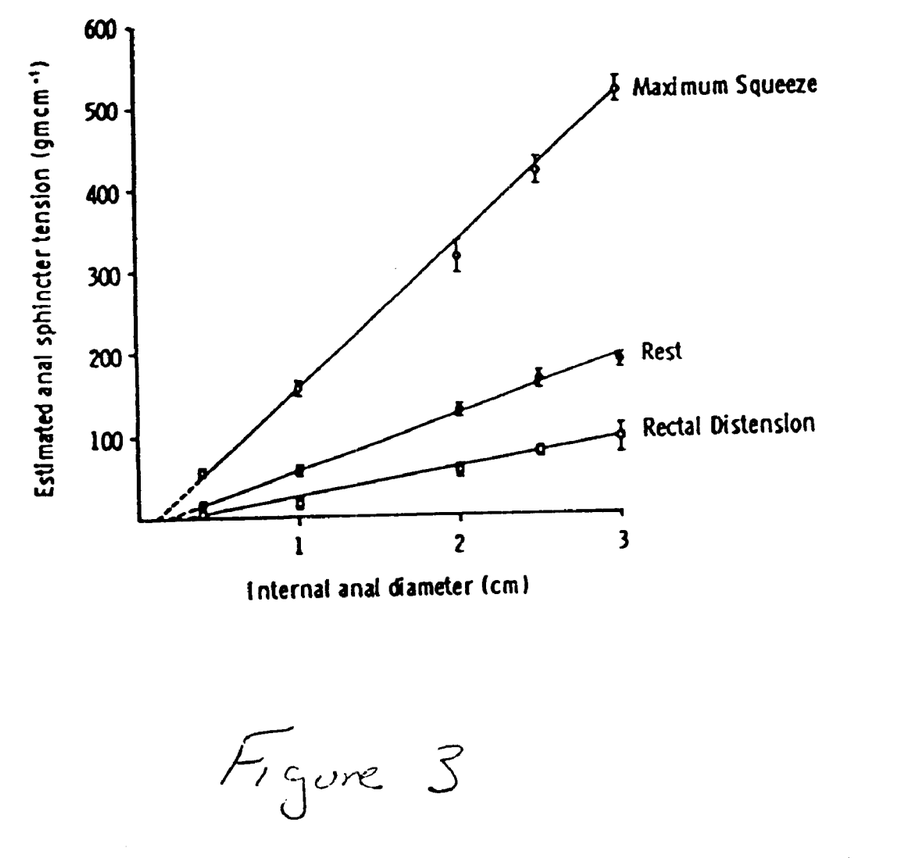
FIG. 3 shows the relationship between anal sphincter tension and diameter of the anal probe serving as a sphincter tension inducer for 16 healthy males (aged 20–76 years, median 36). Each point represents mean ± SEM of 16 observations (0.4 cm, 1 cm, and 2 cm diameter points), 9 observations (2.5 cm diameter points), or 7 observations (3.0 diameter points).

The diameter of the device is an important feature for its effectiveness since the diameter generally influences the values of the pressure that can be achieved in the anal canal by the internal sphincter constriction and by the maximum pelvic muscle contraction. For instance, see FIG. 3, taken from Gibbons et al., "Role of Anal Cushions in Maintaining Continence", The Lancet, Apr. 19, 1986, Vol. 1, pages 886–887 (especially FIG. 1 on page 887). During testing of the device, when probes of different diameters, ranging from 0.3 cm to 3 cm, were inserted into a human anal canal and the established anal sphincter tensions were measured, it was found that the sphincter tension achieved was in proportion to the diameter of the probe inserted. The general finding was that the wider the diameter of the probe, the higher was the sphincter tension. The internal sphincter tension theoretically reaches a zero value when the anal canal is empty.

At rest, the involuntary internal sphincter tension contributes about 7 mm Hg pressure when the anal canal is distended with a probe of 0.3 cm wide in diameter, about 37 mm Hg when the probe is increased to 1 cm, about 44 mm Hg when the probe is 2 cm and about 132 mm Hg when the probe is 3 cm in diameter.

However, irrespective of the diameter of the device, the patient's intentional pelvic muscle contraction can more than double the tension achieved by internal sphincter constriction alone when at rest. The combined effects of the involuntary internal sphincter constriction and the voluntary external sphincter squeeze on average may lead to a high anal pressure of 44 mm Hg when the anal canal is distended to 0.3 cm in diameter, 125 mm Hg at 1 cm distension, 228 mm Hg at 2 cm distension and 385 mm Hg at 3 cm distension (deduced from data reported by Gibbons' article in Lancet I:886–888, 1986). In a normal adult, since there are no capillaries between the arterioles and the venous channels in the anal cushions, the arteriolar blood pressure varies widely and may range from 40 to 120 mm Hg in this region during the systolic-diastolic cycle, depending on the postural position of the patient and on the local conditions that may affect the functions of the arteriolar smooth muscle cells. The venous pressure is about 32 mm Hg at this level when the patient is in the standing position. In the recumbent position, the venous pressure in the vascular plexuses of the anal canal varies greatly, probably between about 7.5 mm Hg and 32 mm Hg. In order to force the blood out of the venous channels of the dilated plexuses in the wall of the anal canal, a pressure above 32 mm Hg would have to be generated by the sphincter is the patient is in an upright position. But an even higher sphincter tension may be required to overcome the pressure of the arteriolar blood which may refill the collapsed venous channels.

A device having a 12 mm outer diameter can induce a sum of involuntary and voluntary sphincter pressures up to 147 mm Hg (200 g per cm$^2$) between the rigid rod and the internal sphincter. This pressure is more than adequate to force the blood in the engorged submucosal and subepithelial venous channels back into the systemic circulation and prevents them from refilling. Although greater diameters will generate a higher sphincter tension, insertion of a rod having a diameter greater than 2 cm will likely cause an undesirably high degree of discomfort in the anal canal with hemorrhoidal disease.

Consequently, the device should have an outer diameter of between about 5 mm and about 30 mm (and preferably between 10 mm and about 25 mm, and most preferably between about 12 mm and about 20 mm) at least at the portion or area to be in contact with the anal canal. These diameter ranges should be sufficient to provide adequate sphincter tension while remaining reasonably comfortable and safe for the user. In addition the device preferably measures between about 4 cm and about 10 cm, and preferably at least about 6 cm, in length from the anal verge after complete insertion, excluding the length contributed by the leading end. In other words, the portion of the device inserted into the anal canal should be between about 4 cm and about 10 cm in length, and preferably about 6 cm in length. The appropriate length is determined by the length of the anal canal, which usually measures about 3–4 cm long (measuring from the anal verge to the pectinate line). Basically, the device must be longer than the anal canal in order to effectively push the cushions up above the anal canal, especially when the voluntary squeezing action is applied by the patient. If the device is not longer than the anal canal, the pelvic muscle and the external sphincter then may create a tendency to cause a downward displacement of the device during treatment.

As noted above, the device preferably has a generally cylindrical shape and a smooth surface for easy and comfortable insertion into the anal canal. The leading or top end of the device is preferably conically shaped, such as an inverted cup, a dome, half of a ball, a bullet head, or a cone for easy insertion into the closed anal canal. The trailing or bottom end preferably includes a stopping portion for controlling the extent of insertion of the device into the anal canal, which may be part of or attached to the device. For instance, the stopping portion may comprise a stopping means, a flange, a flap, or the like, which prevents the device from advancing too far or gliding into the rectum in its entirety.

Figure 1:
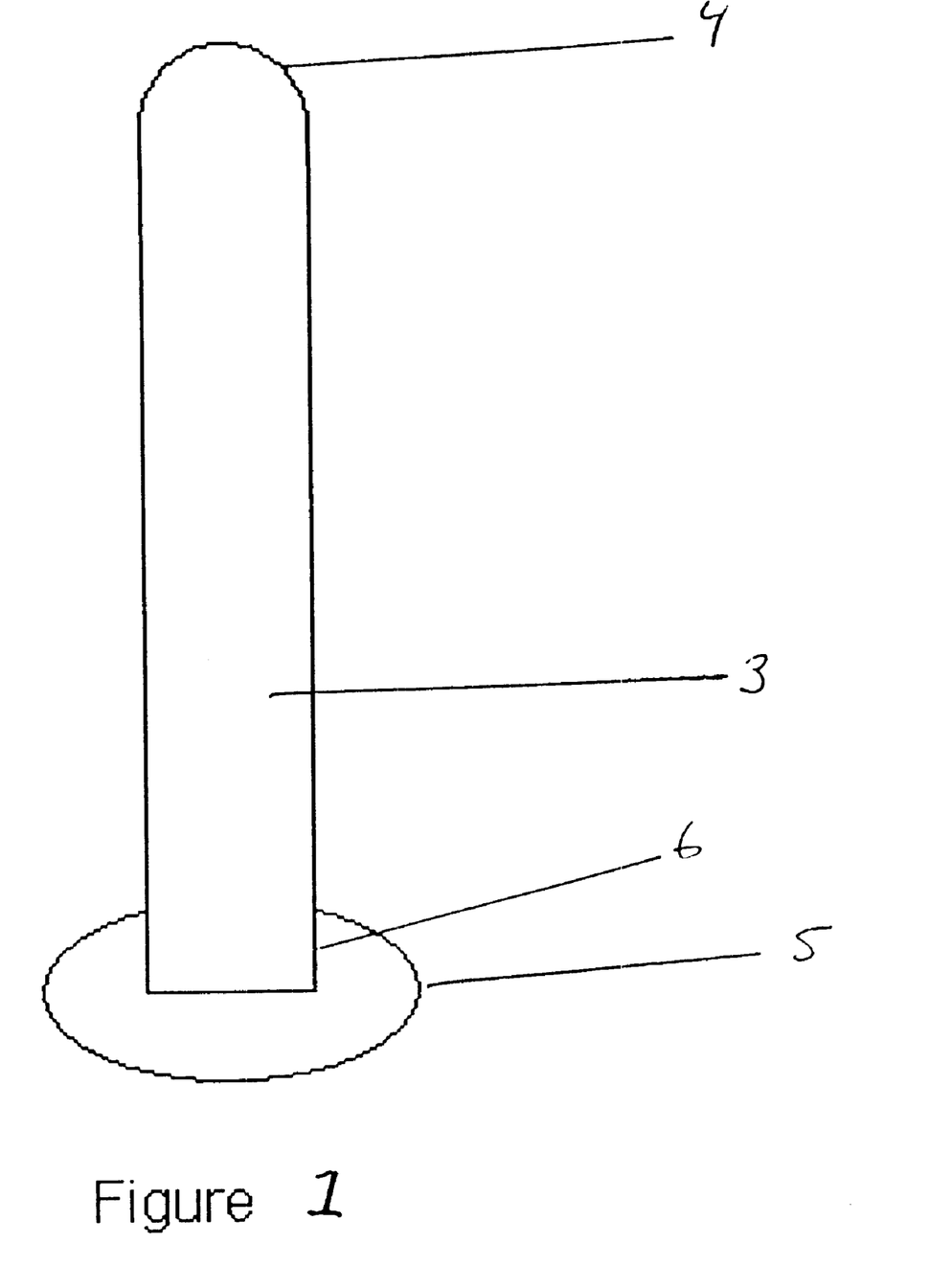
FIG. 1 shows one embodiment of the device of the invention.

One version of this embodiment is depicted in FIG. 1. There, the rod-like or tubelike device has a substantially cylindrical body portion 3, a leading or top end 4 and a trailing or bottom end 6. An optional stopping portion 5 is shown.

In a preferred embodiment, the device has a hollow portion, a top end that is substantially conical in shape with an opening that is in communication with the hollow portion, a bottom end with an opening that is in communication with the hollow portion, and an injecting implement insertable into the hollow portion through the opening in the bottom end. The hollow portion may be filled completely or partially with lubricating ointment, antibiotics or other topical medicaments, or mixtures of these. For example, filling the hollow portion so that the medicaments fill up about 0.5 cubic cm between the leading end and the top of the injecting implement is generally a sufficient amount to achieve optimal results. Preferably, the outer surface of the device is at least partially coated with a lubricant and, optionally, a medicament. After insertion of the device into the anal canal (preferably at about 1 cm past the anal verge), the injecting implement is pushed toward the leading end of the tube to inject its contents into the anal canal before the device is further advanced into the anal canal. In this way, the device operates similar to a syringe.

Figure 2:
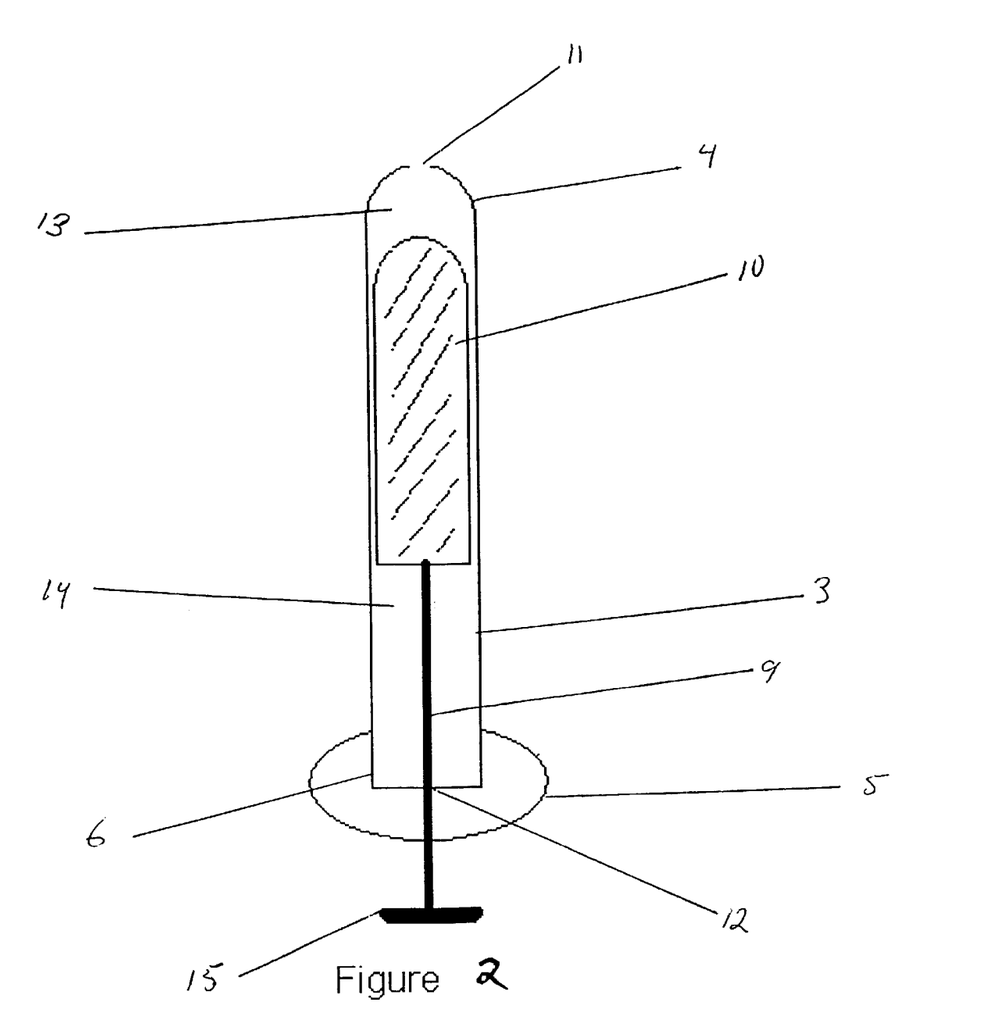
FIG. 2 shows another embodiment of the device of the invention.

One version of this embodiment is shown in FIG. 2. The rod-like or tube-like device has a substantially cylindrical body portion 3, a leading or top end 4 and a trailing or bottom end 6. The body portion 3 contains a hollow portion 14, in which an injecting implement 10 resides, and can be manually or mechanically moved upward or downward by a controller shaft 9 with an optional handle 15. The controller shaft 9 fits slidably through an opening 12 in the trailing end 6. Lubricant and/or medicament may be placed inside the hollow portion 14, for instance above the injecting implement 10 toward the leading end 4 at the region 13. The injecting implement 10 can push the lubricant and/or medicament upward and out of the hollow portion through the opening 11 at the leading end 4. An optional stopping portion 5 is shown.

The method of treatment of hemorrhoids, in its broadest embodiment, is carried out as follows. One of the above-described devices is manually inserted by a patient (or the patient's caregiver) into the patient's anal canal slowly and gently through the anal orifice so that it contacts at least one displaced anal cushion (and preferably all three). The device is advanced until the anal cushion(s) is pushed upward and out of the anal canal, above the pectinate line, in the vicinity where it normally rests. Preferably, where the device includes a stopping portion at the trailing end, the device is to be inserted through the anal orifice until the stopping portion signals the user to cease advancement, such as when the stopping portion reaches the anal verge. Since the anal canal normally measures 3–4 cm long, a device of 6 cm in total length is adequate to accomplish this purpose. The device is maintained in the inserted position long enough to induce and maintain adequate sphincter tensions to cause collapse of the engorged venous channels of the hemorrhoids while keeping the anal cushions in their normal anatomic position above the pecten band. Treatment is usually effective when the insertion is maintained between 5 and 60 minutes (preferably between 25 and 35 minutes, and an average of 30 minutes, for most patients) before the device is removed.

In another preferred embodiment, the device has a syringe-like feature, and includes a hollow interior which contains an amount of a medicament and/or lubricant that may be injected into the anal canal through the top end of the device via an injecting implement, such as is described above. For instance, one version of such a device is depicted in FIG. 2. The method of treatment using this device generally proceeds as follows. As the device is being inserted into the anal canal (preferably at about 1 cm past the anal verge), the injecting implement is pushed through the hollow interior toward the leading end of the device to inject its contents into the anal canal before the device is further advanced into the anal canal.

As noted above, filling the hollow portion so that the medicaments fill up about 0.5 cubic cm between the leading end and the top of the injecting implement is generally a sufficient amount to achieve optimal results. After the lubricant and/or medicament is injected into the anal canal, the device is advanced further into the anal canal until contact is made with at least one displaced anal cushion, and the anal cushion(s) is pushed upward and out of the anal canal, above the pecten line, in the vicinity where it normally rests. Preferably, where the device includes a stopping portion at the trailing end, the device is to be inserted through the anal orifice until the stopping portion signals the user to cease advancement, such as when the stopping portion reaches the anal verge Since the anal canal normally measures 3–4 cm long, a device of 6 cm in total length is adequate to accomplish this purpose. Insertion is maintained for a sufficient time so that internal anal sphincter tension is raised, congestion of the submucosal blood vessels is decreased, and swelling is consequently reduced in the anal cushion(s). At that point, the device may be removed. The anal cushion (s) ought at least temporarily to remain in its relative normal anatomic position above the anal canal. The time to achieve this varies from person to person, and may depend on the severity of the inflammation and other symptoms. However, treatment is usually effective when insertion lasts between about 5 and about 60 minutes (preferably between 25 and 35 minutes, and an average of 30 minutes for most patients).

In this way the lubricant/medicament effectively coats the walls of the anal canal, including the crypts of Morgagni. This embodiment is advantageous because it provides an effective way to spread the injected medicament/lubricant over the inner surface of the anal canal (including the crypts of Morgagni), which is usually a difficult task due to the initial barrier of the skin folds at the anal verge that is generally in apposition to insertion of foreign matter.

For this embodiment, it is preferred that the lubricant and/or medicament contain topically active antibiotics against the opportunistic infective microorganisms, such as various bacteria normally found in the bowel contents. Bacterial infections, often starting in the crypts of Morgagni, may cause a persistent chronic inflammatory reaction. Even a very mild chronic inflammation may render the soft tissue in the pecten band to become so sensitive that the patient may feel a constant urge to empty the bowel since any amount of stool in the lower rectum may serve as a foreign body irritant in these patients. Once injected into the anal canal, the antibiotics in the lubricating ointment can be squeezed between the creases and into the sinuses formed by the rectal mucosa and the modified squamous epithelium during the patient's voluntary pelvic muscle contractions during treatment. It is noted that this method provides an advantage over the use of other currently available rectal suppositories containing medicaments, since rectal suppositories are not suitable for delivering medicaments to the sites deeply seated in the crypts and creases of the anal canal, such as in those of Morgagni or between the papillae at the pectinate line.

For all of the embodiments of the method of treatment, it is preferable that during the period of insertion the patient contracts the pelvic floor muscle as much as possible, as if intending to hold an imminent bowel movement, to squeeze the inserted device in the anal canal. This increases sphincter tension even further.

At the end of treatment the device is slowly and carefully removed. During the period of insertion, the patient must remain stationary, and preferably in a horizontal position, although occasional standing still is also an option. This method of treatment is not suitable for use when the patient is walking, sitting, or moving abruptly.

Before carrying out the treatment, the leading end or top of the device is preferably copiously coated with a lubricating ointment for easy and painless insertion. The ointment may contain any known lubricant, such as petrolatum, cocoa butter, KY jelly, or other non-irritant vegetable oils. The ointment may also contain antibacterial antibiotics (such as one or more of Polymyxin B, Bacitracin and Neomycin), anti-fungal drugs, corticosteroids and local anesthetics, if desired.

After treatment and removal of the device from the anal canal, if possible the patient should remain in a comfortable position (preferably horizontal) for a few additional hours. This allows the internal sphincter muscle time to relax, leading to reduction of the anal canal tension without refilling the collapsed venous channels in the anal canal with blood. Therefore, it is most convenient for the patient to schedule his or her bowel movement in the evening. In this latter case, the patient can have an overnight bed rest after a bowel movement, a warm bath and a course of the treatment.

To maximize the effectiveness of this hemorrhoid treatment, it is preferred that after each defecation and before bedtime the patient gently washes the perianal area clean. This can be best accomplished with lying down horizontally in a tub filled with warm water for about 30 minutes. Before treatment, any hemorrhoids protruding from the anal verge may be reduced using the fingers. After the perianal area is dried, the treatment of the invention may be commenced.

One of the main goals of the invention is to assist in restoring the normal resting anatomic relationship of the various components of the anal canal, namely collapsing the engorged venous plexuses, reducing the mucosal edema, and restoring the anal cushions to their normal anatomic position above the pecten, especially after the act of defecation which invariably causes outward and downward rotation of the anal cushions. These novel devices and methods of treatment are advantageous in that the natural repair processes (such as absorption of the edematous fluid and inflammatory exudate, organization of the local hemorrhage and formation of scar tissue with deposition of newly formed collagen fibers) taking place while the anal cushions are held in position above the pecten in a closed and empty anal canal favor interrupting of the vicious cycle of the key events which led to the appearance and perpetuation of the hemorrhoidal disease.

In order to assist in understanding the invention, the relevant elements in the anatomy of the human anal canal and the essentials in the pathogenesis of the hemorrhoidal disease are briefly reviewed as follows.

The anal canal is a 3–4 cm long passage from the end of the rectum to the outer cutaneous anal orifice, namely from the anorectal line to the anal verge. (For instance, see Philip Thorek: Anatomy in Surgery, Third Edition, Springer-Verlag, New York, 1985, especially at page 491.) Normally, the anal canal is closed and empty because of the constant tension of the sphincters around it and the apposition of the vascular anal cushions at its upper opening, except when stool is being passed. Looking through an anoscope from below, the following four important surface landmarks can be recognized in the anal canal:

1) The anocutaneous line, also referred to as the anal verge, normally is in a state of apposition due to the involuntary action of the corrugator muscle of the anal skin which throws the squamous epithelium into folds.
2) Hilton's line, which lies halfway between the anal verge and the more superior pectinate line, marks the sharp non-muscular interval which exists between the superiorly located internal sphincter and the inferiorly located external sphincter.
3) The pectinate line, also referred to as the dentate line, representing the junction where the glandular rectal mucosa meets the modified squamous epithelium. This line exhibits a comb-like arrangement brought about by the anal papillae which are continuous above with the columns of Morgagni. The bases of the anal papillae are connected by irregular folds which are known as anal valves, thus forming small pockets between the vertical columns. The small pockets are known as the crypts of Morgagni.

The narrow zone between Hilton's line and the pectinate line is called the "pecten", which is covered by a modified squamous epithelium, highly sensitive to pain, and involved in about 85% of all proctologic diseases.

4) The anorectal junction which lies about 1.5 cm above the pectinate line when the anal canal is empty is not sharply demarcated. It represents an imaginary line where the rectum takes a 90-degree turn toward the back to become the upper portion of the anal canal.

Beneath the epithelial lining of the anal canal, there are rich plexuses of vascular tissue composed of blood vessels connecting arteries to veins without intervening capillaries. These vascular plexuses are most prominent under the glandular mucosa (in the submucosa) in the upper part of the anal canal above the pecten. In this location, these vascular plexuses and the covering mucosa form three cushions protruding from the wall of the anal canal into the lumen. These three anal cushions are sometimes referred to as "hemorrhoidal pads" which are strategically positioned at approximately 3, 7 and 11 o'clock circumferentially. The anal cushions tend to hold the mucosa in apposition by their surface secretory function. The vascular cushions themselves are easily distensible. They are usually compressed by high sphincter pressures, but expand to keep the anal canal closed when anal pressures fall. Anal cushions play an important role in keeping the anal canal closed. This important function can be illustrated by the fact that surgical hemorrhoidectomy, in which the enlarged and prolapsed anal cushions are excised, may be complicated by anal soiling even in the presence of normal sphincter pressures and normal anal ultrasonography. The roles played by the anal cushions in the maintenance of anal continence and in the pathogenesis of hemorrhoidal disease have not received adequate attention by many physicians treating hemorrhoidal disease. (See Hass, P A, Fox, T A, Jr. and Haas, G P: The Pathogenesis of Hemorrhoids. Diseases of the Colon and Rectum. 27:442–450, 1984; Gibbons, C P, Trowbridge, E A, Bannister, J J and Read, N W: Role of Anal Cushions in Maintaining Continence. Lancet I: 886–888, 1986.)

In young persons, the submucosal blood vessels in the anal cushions are well supported by connective tissue fibers, namely collagen and elastic fibers. The collagen fibers anchor the anal mucosa and the blood vessels firmly to the internal sphincter and to the longitudinal smooth muscle coat of the terminal rectum. Around age 30, the connective tissue fibers start to disintegrate, and the veins become distended. In the older age group, the anchoring connective tissue system degenerates and the fibers are broken loose.

During the act of defecation with relaxation of the internal sphincter normally induced by rectal distention and passing of a bolus of stool, there is always an outward, downward rotation of the anal cushions and the pecten. In the child and healthy young adult, the anal cushions and the pecten will rotate back to their normal positions after defecation. (See Keighley, M R B and Williams N S : Surgery of the Anus, Rectum and Colon. Second Edition, W. B. Saunders, London, 1999, page 354.). However, in the older age group, the cushions and the pecten do not return spontaneously or quickly to their normal position after defecation. Or they may do so only after a period of bed rest when the internal sphincter tension is reduced and the venous blood in the engorged plexuses has returned to the systemic circulation.

These downward protruding congested hypertrophic anal cushions are generally referred to in this patent as "hemorrhoids", which are a common finding during routine physical examination in the older age group and are largely symptom-less. Consequently, the appearance of "hemorrhoids" is considered to be a normal aging phenomenon. No treatment is indicated in most patients. Only when the enlarged anal cushions become symptomatic, should the term "hemorrhoidal disease" be applied, and at that point the condition calls for medical attention. Among many factors that contribute to the development of hemorrhoidal disease are errors in bowel habits, such as the patient's insistence on having at least one bowel movement daily, neglect of the first urge to defecate, insistence on trying to pass the last portion of stool from the rectum or anal canal, or other circumstances leading to prolonged straining. Prolonged straining during defecation, especially when the sphincters are not relaxed in the absence of an adequately voluminous bolus of feces in the rectum serving as a proper stimulus, keeps the vascular anal cushions outside the lower edge of the internal sphincter which in turn constricts and congests them. As a result, a vicious cycle of voluntary or involuntary sphincter constriction, increasing enlargement of the congested anal cushions, and an irritating foreign body sensation is established in the upper portion of the anal canal. Eventually, the prolapsing mass will include the sensitive zone covered by the modified squamous epithelium of the pecten and its underlying blood vessels. Congestion, hypertrophy and surface erosion of this downward protruding mass in the anal canal, commonly referred to as "internal hemorrhoids", may lead to local infection, pain, bleeding and thrombosis. The deranged anatomic relationship of the vascular anal cushions and the pecten band often cause leakage of rectal fluids or soiling. Bacterial infection beginning in the crypts of Morgagni can also play an important role in the pathogenesis of "hemorrhoidal disease".

The passage of stool, especially a hard stool with prolonged straining, has a shearing effect on the vascular submucosa. Therefore, as a general measure the patient should avoid prolonged straining during defecation by correcting his or her errors in bowel habits and by adopting a bulk-forming diet. Diarrheagenic foods or drink should also be avoided.

Of course, it is advised that any person suffering from hemorrhoids should first consult a physician to verify diagnosis of a minor hemorrhoidal disease of a first-, second- or third-degree. As noted above, advanced stages of hemorrhoidal may need invasive therapies. Preferably, the patient is familiarized with the normal aging process of the tissues in the anal canal and the pathogenesis of the hemorrhoidal disease. The patient should know that one of the goals of treating minor hemorrhoidal disease using this device and method is to restore the normal anatomic conditions of the anal canal to prevent recurrences of the complications of a normal aging process and/or to prevent a minor complication from progressing into an advanced stage which would need invasive therapies.

The invention has been described above in its preferred embodiments, which are exemplary only. Numerous modifications can be made to the disclosed embodiments without departing from the spirit of the invention. It is, therefore, the intention that the invention not be limited by the details of the preferred embodiments, as would be understood by someone having ordinary skill in this art.

All of the references cited herein, including patents and journal articles, are incorporated by reference in their entirety.

What is claimed is:

1. A method for treating hemorrhoidal disease whereby at least one of three anal cushions is swollen and displaced from its normal anatomical position above the anal canal and is at least partially descended into the anal canal, by increasing total sphincter tension in the anal canal, pushing at least one anal cushion above the anal canal, and collapsing engorged blood channels in the wall of the anal canal, which method comprises the steps of:

pushing the at least one anal cushion above the anal canal into its normal anatomical position by inserting a device having a substantially cylindrical shape and a substantially smooth surface into the anal canal so that it induces involuntary internal sphincter constriction and providing a counter-compressor for the voluntary external sphincter muscle contraction to increase the total sphincter tension in the anal canal, wherein the device has a diameter of between about 5 mm and about 30 mm at the portion in contact with the wall of the anal canal;

(b) maintaining insertion of the device for sufficient time so that engorged blood channels in the wall of the anal canal collapse; and (c) removing the device from the anal canal.

2. The method of claim 1, wherein the device is coated with a lubricant or a medicament, or both, prior to step (a).

3. The method of claim 2, wherein the lubricant is selected from the group consisting of petroleum jelly, KY jelly, cocoa butter, vegetable oils, and mixtures thereof.

4. The method of claim 2, wherein the medicament is selected from the group consisting of antibiotics, corticosteroids, anesthetics, anti-fungal compositions, and mixtures thereof.

5. The method of claim 1, wherein the portion of the device inserted into the anal canal is between about 4 cm and about 10 cm in length.

6. The method of claim 5, wherein the portion of the device inserted into the anal canal is about 6 cm in length.

7. The method of claim 1, wherein the device further includes a stopping portion.

8. The method of claim 7, wherein the stopping portion is formed of a stopping means, a flange, a flap, or a combination thereof.

9. The method of claim 1, wherein the device has a diameter of between about 12 mm and about 20 mm at the portion in contact with the wall of the anal canal.

10. The method of claim 1, wherein the device has a conical head.

11. The method of claim 1, wherein insertion of the device is maintained between about 5 minutes and about 1 hour.

12. The method of claim 1, wherein insertion of the device is maintained between about 25 minutes and about 35 minutes.

13. A method for treating hemorrhoidal disease whereby at least one of three anal cushions is swollen and displaced from its normal anatomical position above the anal canal and is at least partially descended into the anal canal, by increasing total sphincter tension in the anal canal, pushing at least one anal cushion above the anal canal, and collapsing engorged blood channels in the wall of the anal canal, which method comprises the steps of pushing the at least one anal canal cushion above the anal canal into its normal anatomical position by inserting a device having a substantially cylindrical shape and a substantially smooth surface into the anal canal so that it induces involuntary internal sphincter constriction and provides a counter-compressor for the voluntary external sphincter muscle contraction to increase the total sphincter tension in the anal canal, wherein the device has a hollow portion containing lubricant or medicament, or both, a top end that is substantially conical in shape with an opening that is in communication with the hollow portion, a bottom end with an opening that is in communication with the hollow portion, and an injecting implement insertable into the hollow portion through the opening in the bottom end, and wherein the device has a diameter of between about 5 mm and about 30 mm at the portion in contact with the wall of the anal canal;

wherein as the device is being inserted into the anal canal, the lubricant or medicament, or both, is injected by the injecting implement through the opening in the top end into the anal canal;

(b) maintaining insertion of the device for sufficient time so that engorged blood channels in the wall of the anal canal are collapsed; and (c) removing the device from the anal canal.

14. The method of claim 13, wherein the portion of the device inserted into the anal canal is between about 4 cm and about 10 cm in length.

15. The method of claim 14, wherein the portion of the device inserted into the anal canal is about 6 cm in length.

16. The method of claim 13, wherein the device further includes a stopping portion.

17. The method of claim 16, wherein the stopping portion is formed of a stopper means, a flange, a flap, or a combination thereof.

18. The method of claim 13, wherein the lubricant is selected from the group consisting of petroleum jelly, cocoa butter, vegetable oils, and mixtures thereof.

19. The method of claim 13, wherein the medicament is selected from the group consisting of antibiotics, corticosteroids, anesthetics, antifungal compositions, and mixtures thereof.

20. The method of claim 13, wherein the device has a diameter of between about 10 mm and about 25 mm at the portion in contact with the wall of the anal canal.

21. The method of claim 13, wherein the device has a diameter of between about 12 mm and about 20 mm at the portion in contact with the wall of the anal canal.

22. The method of claim 13, wherein the device has a conical head.

23. The method of claim 13, wherein insertion of the device is maintained between about 5 minutes and about 1 hour.

24. The method of claim 13, wherein insertion of the device is maintained between about 25 minutes and about 35 minutes.

* * * * *